(12) United States Patent
Ferree et al.

(10) Patent No.: US 8,277,507 B2
(45) Date of Patent: Oct. 2, 2012

(54) SPACERLESS ARTIFICIAL DISC REPLACEMENTS

(75) Inventors: Bret A. Ferree, Cincinnati, OH (US); David Tompkins, Milford, OH (US)

(73) Assignee: SpineCore, Inc., Allendale, NJ (US)

( * ) Notice: Subject to any disclaimer, the term of this patent is extended or adjusted under 35 U.S.C. 154(b) by 52 days.

(21) Appl. No.: 12/789,925

(22) Filed: May 28, 2010

(65) Prior Publication Data

US 2010/0241233 A1 Sep. 23, 2010

Related U.S. Application Data (63) Continuation of application No. 11/194,786, filed on Aug. 1, 2005, now abandoned, and a continuation of application No. 10/413,028, filed on Apr. 14, 2003, now abandoned.

(60) Provisional application No. 60/449,642, filed on Feb. 24, 2003, provisional application No. 60/372,520, filed on Apr. 12, 2002.

(51) Int. Cl.
*A61F 2/44* (2006.01)
(52) U.S. Cl. .................. 623/17.14; 623/17.15
(58) Field of Classification Search .......... None
See application file for complete search history.

(56) References Cited

U.S. PATENT DOCUMENTS

| 916,421 | A | 3/1909 | Crittenden |
|---|---|---|---|
| 2,193,122 | A | 3/1940 | Crabbs |
| 2,669,896 | A | 2/1954 | Clough |
| 2,774,350 | A | 12/1956 | Cleveland, Jr. |
| 3,086,208 | A | 4/1963 | Eby |
| 3,278,107 | A | 10/1966 | Rygg |
| 3,486,505 | A | 12/1969 | Morrison |
| 3,604,487 | A | 9/1971 | Gilbert |
| 3,867,728 | A | 2/1975 | Stubstad et al. |
| 3,872,519 | A | 3/1975 | Giannestras et al. |
| 4,021,864 | A | 5/1977 | Waugh |
| 4,105,407 | A | 8/1978 | Sanderson |
| 4,217,902 | A | 8/1980 | March |
| 4,263,903 | A | 4/1981 | Griggs |
| 4,296,751 | A | 10/1981 | Blake, III et al. |
| 4,303,001 | A | 12/1981 | Trungold |
| 4,309,777 | A | 1/1982 | Patil |
| 4,457,484 | A | 7/1984 | Hameister |
| 4,528,980 | A | 7/1985 | Kenna |
| 4,531,517 | A | 7/1985 | Forte et al. |
| 4,566,466 | A | 1/1986 | Ripple et al. |
| 4,605,417 | A | 8/1986 | Fleischauer |
| 4,733,657 | A | 3/1988 | Kluger |
| 4,759,766 | A | 7/1988 | Buettner-Janz et al. |
| 4,759,769 | A | 7/1988 | Hedman et al. |
| 4,874,314 | A | 10/1989 | Fleer et al. |

(Continued)

FOREIGN PATENT DOCUMENTS

DE 3023492 A1 2/1982

(Continued)

*Primary Examiner* — David H Willse
*Assistant Examiner* — Javier Blanco
(74) *Attorney, Agent, or Firm* — Lerner, David, Littenberg, Krumholz & Mentlik, LLP (57) ABSTRACT

Spacerless artificial disc replacements (ADR) are disclosed. One preferred embodiment includes two saddle-shaped components to facilitate more normal spinal flexion, extension, and lateral bending while limit axial rotation, thereby protecting the facet joints and the annulus fibrosus (AF). Either or both of the superior and inferior components are made of a hard material such as chrome cobalt, titanium, or a ceramic including alumina, zirconia, or calcium phosphate. The articulating surfaces of the ADR are also preferably highly polished to reduce friction between the components. Metals, alloys or other materials with shape-memory characteristics may also prove beneficial.

9 Claims, 5 Drawing Sheets

U.S. PATENT DOCUMENTS

| | | |
|---|---|---|
| 4,917,704 A | 4/1990 | Frey et al. |
| 4,932,969 A | 6/1990 | Frey et al. |
| 4,955,908 A | 9/1990 | Frey et al. |
| 4,969,907 A | 11/1990 | Koch et al. |
| 4,997,432 A | 3/1991 | Keller |
| 5,002,576 A | 3/1991 | Fuhrmann et al. |
| 5,030,219 A | 7/1991 | Matsen, III et al. |
| 5,034,254 A | 7/1991 | Cologna et al. |
| 5,112,178 A | 5/1992 | Overhues et al. |
| 5,122,130 A | 6/1992 | Keller |
| 5,192,327 A | 3/1993 | Brantigan |
| 5,236,460 A | 8/1993 | Barber |
| 5,246,458 A | 9/1993 | Graham |
| 5,258,007 A | 11/1993 | Spetzler et al. |
| 5,258,031 A | 11/1993 | Salib et al. |
| 5,269,790 A | 12/1993 | Funatsu |
| 5,306,308 A | 4/1994 | Gross et al. |
| 5,314,477 A | 5/1994 | Marnay |
| 5,364,399 A | 11/1994 | Lowery et al. |
| 5,370,697 A | 12/1994 | Baumgartner |
| 5,376,120 A | 12/1994 | Sarver et al. |
| 5,401,269 A | 3/1995 | Buttner-Janz et al. |
| 5,405,400 A | 4/1995 | Linscheid et al. |
| 5,425,773 A | 6/1995 | Boyd et al. |
| 5,443,514 A | 8/1995 | Steffee |
| 5,458,641 A | 10/1995 | Ramirez Jimenez |
| 5,458,642 A | 10/1995 | Beer et al. |
| 5,507,816 A | 4/1996 | Bullivant |
| 5,514,180 A | 5/1996 | Heggeness et al. |
| 5,522,900 A | 6/1996 | Hollister |
| 5,534,029 A | 7/1996 | Shima |
| 5,548,642 A | 8/1996 | Diethorn |
| 5,549,690 A | 8/1996 | Hollister et al. |
| 5,556,431 A | 9/1996 | Buttner-Janz |
| 5,556,432 A | 9/1996 | Kubein-Meesenburg et al. |
| 5,562,736 A | 10/1996 | Ray et al. |
| 5,562,738 A | 10/1996 | Boyd et al. |
| 5,593,456 A | 1/1997 | Merlette |
| 5,599,279 A | 2/1997 | Slotman et al. |
| 5,645,605 A | 7/1997 | Klawitter |
| 5,653,762 A | 8/1997 | Pisharodi |
| 5,674,296 A | 10/1997 | Bryan et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,720,751 A | 2/1998 | Jackson |
| 5,732,992 A | 3/1998 | Mauldin |
| 5,733,290 A | 3/1998 | McCue et al. |
| 5,755,796 A | 5/1998 | Ibo et al. |
| 5,769,856 A | 6/1998 | Dong et al. |
| 5,776,198 A | 7/1998 | Rabbe et al. |
| 5,782,830 A | 7/1998 | Farris |
| 5,782,832 A | 7/1998 | Larsen et al. |
| 5,827,328 A | 10/1998 | Buttermann |
| 5,860,990 A | 1/1999 | Nobles et al. |
| 5,865,846 A | 2/1999 | Bryan et al. |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,910,141 A | 6/1999 | Morrison et al. |
| 5,916,267 A | 6/1999 | Tienboon |
| 5,926,685 A | 7/1999 | Krebs et al. |
| 5,928,284 A | 7/1999 | Mehdizadeh |
| 5,976,186 A | 11/1999 | Bao et al. |
| 5,983,889 A | 11/1999 | Thomas |
| 5,989,291 A | 11/1999 | Ralph et al. |
| 5,989,294 A | 11/1999 | Marlow |
| 6,001,030 A | 12/1999 | Delaney |
| 6,001,130 A | 12/1999 | Bryan et al. |
| 6,019,792 A | 2/2000 | Cauthen |
| 6,039,763 A | 3/2000 | Shelokov |
| 6,050,999 A | 4/2000 | Paraschac et al. |
| 6,051,751 A | 4/2000 | Sioshansi et al. |
| 6,063,121 A | 5/2000 | Xavier et al. |
| 6,066,174 A | 5/2000 | Farris |
| 6,066,175 A | 5/2000 | Henderson et al. |
| 6,080,155 A | 6/2000 | Michelson |
| 6,093,205 A | 7/2000 | McLeod et al. |
| 6,093,207 A | 7/2000 | Pisharodi |
| 6,096,080 A | 8/2000 | Nicholson et al. |
| 6,106,557 A | 8/2000 | Robioneck et al. |
| 6,111,222 A | 8/2000 | Hattori |
| 6,113,602 A | 9/2000 | Sand |
| 6,113,637 A | 9/2000 | Gill et al. |
| 6,113,638 A | 9/2000 | Williams et al. |
| 6,113,639 A | 9/2000 | Ray et al. |
| 6,136,031 A | 10/2000 | Middleton |
| 6,139,550 A | 10/2000 | Michelson |
| 6,143,012 A | 11/2000 | Gausepohl |
| 6,146,421 A | 11/2000 | Gordon et al. |
| 6,156,067 A | 12/2000 | Bryan et al. |
| 6,159,215 A | 12/2000 | Urbahns et al. |
| 6,162,252 A | 12/2000 | Kuras et al. |
| 6,174,311 B1 | 1/2001 | Branch et al. |
| 6,179,873 B1 | 1/2001 | Zientek |
| 6,179,874 B1 | 1/2001 | Cauthen |
| 6,190,413 B1 | 2/2001 | Sutcliffe |
| 6,190,414 B1 | 2/2001 | Young et al. |
| 6,193,757 B1 | 2/2001 | Foley et al. |
| 6,213,055 B1 | 4/2001 | Willinger et al. |
| 6,214,005 B1 | 4/2001 | Benzel et al. |
| 6,214,049 B1 | 4/2001 | Gayer et al. |
| 6,217,615 B1 | 4/2001 | Sioshansi et al. |
| 6,224,607 B1 | 5/2001 | Michelson |
| 6,228,023 B1 | 5/2001 | Zaslavsky et al. |
| 6,228,118 B1 | 5/2001 | Gordon |
| 6,231,609 B1 | 5/2001 | Mehdizadeh |
| 6,235,034 B1 | 5/2001 | Bray |
| 6,235,059 B1 | 5/2001 | Benezech et al. |
| 6,235,060 B1 | 5/2001 | Kubein-Meesenburg et al. |
| 6,241,732 B1 | 6/2001 | Overaker et al. |
| 6,241,769 B1 | 6/2001 | Nicholson et al. |
| 6,261,293 B1 | 7/2001 | Nicholson et al. |
| 6,261,296 B1 | 7/2001 | Aebi et al. |
| 6,261,324 B1 | 7/2001 | Merlette |
| 6,277,149 B1 | 8/2001 | Boyle et al. |
| 6,280,458 B1 | 8/2001 | Boche et al. |
| 6,296,647 B1 | 10/2001 | Robioneck et al. |
| 6,296,665 B1 | 10/2001 | Strnad et al. |
| 6,319,257 B1 | 11/2001 | Carignan et al. |
| 6,325,828 B1 | 12/2001 | Dennis et al. |
| 6,332,887 B1 | 12/2001 | Knox |
| 6,342,057 B1 | 1/2002 | Brace et al. |
| 6,348,071 B1 | 2/2002 | Steffee et al. |
| 6,368,350 B1 | 4/2002 | Erickson et al. |
| 6,375,682 B1 | 4/2002 | Fleischmann et al. |
| 6,395,030 B1 | 5/2002 | Songer et al. |
| 6,395,032 B1 | 5/2002 | Gauchet |
| 6,395,035 B2 | 5/2002 | Bresina et al. |
| 6,398,815 B1 | 6/2002 | Pope et al. |
| 6,413,259 B1 | 7/2002 | Lyons et al. |
| 6,416,551 B1 | 7/2002 | Keller |
| 6,425,920 B1 | 7/2002 | Hamada |
| 6,428,544 B1 | 8/2002 | Ralph et al. |
| 6,432,106 B1 | 8/2002 | Fraser |
| 6,436,102 B1 | 8/2002 | Ralph et al. |
| 6,440,139 B2 | 8/2002 | Michelson |
| 6,440,168 B1 | 8/2002 | Cauthen |
| 6,447,547 B1 | 9/2002 | Michelson |
| 6,461,359 B1 | 10/2002 | Tribus et al. |
| 6,468,310 B1 | 10/2002 | Ralph et al. |
| 6,471,725 B1 | 10/2002 | Ralph et al. |
| 6,478,796 B2 | 11/2002 | Zucherman et al. |
| 6,478,800 B1 | 11/2002 | Fraser et al. |
| 6,478,801 B1 | 11/2002 | Ralph et al. |
| 6,488,710 B2 | 12/2002 | Besselink |
| 6,499,595 B1 | 12/2002 | Petricca |
| 6,517,580 B1 | 2/2003 | Ramadan et al. |
| 6,520,996 B1 | 2/2003 | Manasas et al. |
| 6,524,312 B2 | 2/2003 | Landry et al. |
| 6,527,320 B1 | 3/2003 | Gregg |
| 6,527,786 B1 | 3/2003 | Davis et al. |
| 6,527,804 B1 | 3/2003 | Gauchet et al. |
| 6,527,806 B2 | 3/2003 | Ralph et al. |

| Patent Number | Date | Inventor(s) |
|---|---|---|
| 6,540,785 B1 | 4/2003 | Gill et al. |
| 6,554,864 B2 | 4/2003 | Ralph et al. |
| 6,562,047 B2 | 5/2003 | Ralph et al. |
| 6,562,073 B2 | 5/2003 | Foley |
| 6,572,653 B1 | 6/2003 | Simonson |
| 6,576,017 B2 | 6/2003 | Foley et al. |
| 6,579,290 B1 | 6/2003 | Hardcastle et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,468 B1 | 6/2003 | Gauchet |
| 6,589,247 B2 | 7/2003 | McGahan et al. |
| 6,592,624 B1 | 7/2003 | Fraser et al. |
| 6,599,291 B1 | 7/2003 | Foley et al. |
| 6,602,292 B2 | 8/2003 | Burkinshaw |
| 6,607,558 B2 | 8/2003 | Kuras |
| 6,607,559 B2 | 8/2003 | Ralph et al. |
| 6,610,092 B2 | 8/2003 | Ralph et al. |
| 6,610,093 B1 | 8/2003 | Pisharodi |
| 6,623,525 B2 | 9/2003 | Ralph et al. |
| 6,632,091 B1 | 10/2003 | Cise et al. |
| 6,641,614 B1 | 11/2003 | Wagner et al. |
| 6,645,248 B2 | 11/2003 | Casutt |
| 6,645,249 B2 | 11/2003 | Ralph et al. |
| 6,652,233 B2 | 11/2003 | Otake |
| 6,652,525 B1 | 11/2003 | Assaker et al. |
| 6,652,533 B2 | 11/2003 | O'Neil |
| 6,666,866 B2 | 12/2003 | Martz et al. |
| 6,669,699 B2 | 12/2003 | Ralph et al. |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,887 B2 | 1/2004 | Nicholson et al. |
| 6,679,915 B1 | 1/2004 | Cauthen |
| 6,682,562 B2 | 1/2004 | Viart et al. |
| 6,692,495 B1 | 2/2004 | Zacouto |
| 6,706,068 B2 | 3/2004 | Ferree |
| 6,709,439 B2 | 3/2004 | Rogers et al. |
| 6,712,825 B2 | 3/2004 | Aebi et al. |
| 6,716,245 B2 | 4/2004 | Pasquet et al. |
| 6,730,127 B2 | 5/2004 | Michelson |
| 6,740,118 B2 | 5/2004 | Eisermann et al. |
| 6,743,257 B2 | 6/2004 | Castro |
| 6,755,841 B2 | 6/2004 | Fraser et al. |
| 6,770,096 B2 | 8/2004 | Bolger et al. |
| 6,793,678 B2 | 9/2004 | Hawkins |
| 6,796,988 B2 | 9/2004 | Melkent et al. |
| 6,800,093 B2 | 10/2004 | Nicholson et al. |
| 6,827,743 B2 | 12/2004 | Eisermann et al. |
| 6,835,206 B2 | 12/2004 | Jackson |
| 6,837,905 B1 | 1/2005 | Lieberman |
| 6,863,688 B2 | 3/2005 | Ralph et al. |
| 6,863,689 B2 | 3/2005 | Ralph et al. |
| 6,875,213 B2 | 4/2005 | Michelson |
| 6,884,242 B2 | 4/2005 | LeHuec et al. |
| 6,896,676 B2 | 5/2005 | Zubok et al. |
| 6,908,484 B2 | 6/2005 | Zubok et al. |
| 6,918,934 B2 | 7/2005 | Ralph et al. |
| 6,923,814 B1 | 8/2005 | Hildebrand et al. |
| 6,936,071 B1 | 8/2005 | Marnay et al. |
| 6,972,021 B2 | 12/2005 | Raugel |
| 6,972,037 B2 | 12/2005 | Zubok et al. |
| 6,972,038 B2 | 12/2005 | Zubok et al. |
| 6,981,990 B2 | 1/2006 | Keller |
| 6,986,789 B2 | 1/2006 | Schultz et al. |
| 6,991,654 B2 | 1/2006 | Foley |
| 6,994,727 B2 | 2/2006 | Khandkar et al. |
| 6,994,728 B2 | 2/2006 | Zubok et al. |
| 6,994,729 B2 | 2/2006 | Zubok et al. |
| 6,997,954 B2 | 2/2006 | Zubok et al. |
| 6,997,955 B2 | 2/2006 | Zubok et al. |
| 7,022,139 B2 | 4/2006 | Errico et al. |
| 7,056,344 B2 | 6/2006 | Huppert et al. |
| 7,063,725 B2 | 6/2006 | Foley |
| 7,115,132 B2 | 10/2006 | Errico et al. |
| 7,118,579 B2 | 10/2006 | Michelson |
| 7,125,425 B2 | 10/2006 | Foley et al. |
| 7,147,642 B2 | 12/2006 | Grinberg et al. |
| 7,153,303 B2 | 12/2006 | Squires et al. |
| 7,153,304 B2 | 12/2006 | Robie et al. |
| 7,198,643 B2 | 4/2007 | Zubok et al. |
| 7,204,852 B2 | 4/2007 | Marnay et al. |
| 7,226,452 B2 | 6/2007 | Zubok et al. |
| 7,235,104 B2 | 6/2007 | Grinberg et al. |
| 7,238,203 B2 | 7/2007 | Bagga et al. |
| 7,270,679 B2 | 9/2007 | Istephanous et al. |
| 7,300,441 B2 | 11/2007 | Haid et al. |
| 7,320,689 B2 | 1/2008 | Keller |
| 7,537,614 B2 | 5/2009 | Baumgartner et al. |
| 7,637,911 B2 | 12/2009 | Zubok et al. |
| 7,794,465 B2 | 9/2010 | Marik et al. |
| 2001/0005796 A1 | 6/2001 | Zdeblick et al. |
| 2001/0007073 A1 | 7/2001 | Zucherman et al. |
| 2001/0010001 A1 | 7/2001 | Michelson |
| 2001/0012938 A1 | 8/2001 | Zucherman et al. |
| 2001/0016773 A1 | 8/2001 | Serhan et al. |
| 2001/0016774 A1 | 8/2001 | Bresina et al. |
| 2001/0020170 A1 | 9/2001 | Zucherman et al. |
| 2001/0027343 A1 | 10/2001 | Keller |
| 2001/0039452 A1 | 11/2001 | Zucherman et al. |
| 2002/0004683 A1 | 1/2002 | Michelson |
| 2002/0017789 A1 | 2/2002 | Holmes et al. |
| 2002/0035400 A1 | 3/2002 | Bryan et al. |
| 2002/0045901 A1 | 4/2002 | Wagner et al. |
| 2002/0045904 A1 | 4/2002 | Fuss et al. |
| 2002/0062131 A1 | 5/2002 | Gallo |
| 2002/0082597 A1 | 6/2002 | Fraser |
| 2002/0082695 A1 | 6/2002 | Neumann |
| 2002/0082701 A1 | 6/2002 | Zdeblick et al. |
| 2002/0099377 A1 | 7/2002 | Zucherman et al. |
| 2002/0107571 A1 | 8/2002 | Foley |
| 2002/0107572 A1 | 8/2002 | Foley et al. |
| 2002/0111679 A1 | 8/2002 | Zucherman et al. |
| 2002/0111681 A1 | 8/2002 | Ralph et al. |
| 2002/0111682 A1 | 8/2002 | Ralph et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0111686 A1 | 8/2002 | Ralph et al. |
| 2002/0111687 A1 | 8/2002 | Ralph et al. |
| 2002/0116009 A1 | 8/2002 | Fraser et al. |
| 2002/0123750 A1 | 9/2002 | Eisermann et al. |
| 2002/0128714 A1 | 9/2002 | Manasas et al. |
| 2002/0128715 A1 | 9/2002 | Bryan et al. |
| 2002/0143399 A1 | 10/2002 | Sutcliffe |
| 2002/0147450 A1 | 10/2002 | LeHuec et al. |
| 2002/0161375 A1 | 10/2002 | Ralph et al. |
| 2002/0169508 A1 | 11/2002 | Songer et al. |
| 2002/0177897 A1 | 11/2002 | Michelson |
| 2002/0188295 A1 | 12/2002 | Martz et al. |
| 2002/0193880 A1 | 12/2002 | Fraser |
| 2003/0009223 A1 | 1/2003 | Fehling et al. |
| 2003/0009224 A1 | 1/2003 | Kuras |
| 2003/0014057 A1 | 1/2003 | Ralph et al. |
| 2003/0014109 A1 | 1/2003 | Ralph et al. |
| 2003/0014110 A1 | 1/2003 | Ralph et al. |
| 2003/0014111 A1 | 1/2003 | Ralph et al. |
| 2003/0014112 A1 | 1/2003 | Ralph et al. |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023245 A1 | 1/2003 | Ralph et al. |
| 2003/0023309 A1 | 1/2003 | Ralph et al. |
| 2003/0023310 A1 | 1/2003 | Ralph et al. |
| 2003/0028197 A1 | 2/2003 | Hanson et al. |
| 2003/0028249 A1 | 2/2003 | Baccelli et al. |
| 2003/0028252 A1 | 2/2003 | Ralph et al. |
| 2003/0040796 A1 | 2/2003 | Ferree |
| 2003/0040801 A1 | 2/2003 | Ralph et al. |
| 2003/0045939 A1 | 3/2003 | Casutt |
| 2003/0055503 A1 | 3/2003 | O'Neil |
| 2003/0060886 A1 | 3/2003 | Van Hoeck et al. |
| 2003/0065395 A1 | 4/2003 | Ralph et al. |
| 2003/0069586 A1 | 4/2003 | Errico et al. |
| 2003/0069642 A1 | 4/2003 | Ralph et al. |
| 2003/0074064 A1 | 4/2003 | Gerbec et al. |

| | | |
|---|---|---|
| 2003/0074067 A1 | 4/2003 | Errico et al. |
| 2003/0078662 A1 | 4/2003 | Ralph et al. |
| 2003/0078663 A1 | 4/2003 | Ralph et al. |
| 2003/0078664 A1 | 4/2003 | Ralph et al. |
| 2003/0078665 A1 | 4/2003 | Ralph et al. |
| 2003/0078666 A1 | 4/2003 | Ralph et al. |
| 2003/0078667 A1 | 4/2003 | Manasas et al. |
| 2003/0078668 A1 | 4/2003 | Michelson |
| 2003/0083747 A1 | 5/2003 | Winterbottom et al. |
| 2003/0083749 A1 | 5/2003 | Kuslich et al. |
| 2003/0093153 A1 | 5/2003 | Banick et al. |
| 2003/0100949 A1 | 5/2003 | Michelson |
| 2003/0100951 A1 | 5/2003 | Serhan et al. |
| 2003/0109928 A1 | 6/2003 | Pasquet et al. |
| 2003/0120344 A1 | 6/2003 | Michelson |
| 2003/0125748 A1 | 7/2003 | Li et al. |
| 2003/0135213 A1 | 7/2003 | LeHuec et al. |
| 2003/0135278 A1 | 7/2003 | Eckman |
| 2003/0135279 A1 | 7/2003 | Michelson |
| 2003/0149438 A1 | 8/2003 | Nichols et al. |
| 2003/0149482 A1 | 8/2003 | Michelson |
| 2003/0167091 A1 | 9/2003 | Scharf |
| 2003/0167092 A1 | 9/2003 | Foley |
| 2003/0171813 A1 | 9/2003 | Kiester |
| 2003/0176921 A1 | 9/2003 | Lawson |
| 2003/0176922 A1 | 9/2003 | Lawson et al. |
| 2003/0176923 A1 | 9/2003 | Keller et al. |
| 2003/0181982 A1 | 9/2003 | Kuslich |
| 2003/0187453 A1 | 10/2003 | Schlapfer et al. |
| 2003/0187454 A1 | 10/2003 | Gill et al. |
| 2003/0187508 A1 | 10/2003 | Cauthen |
| 2003/0191534 A1 | 10/2003 | Viart et al. |
| 2003/0195632 A1 | 10/2003 | Foley et al. |
| 2003/0199981 A1 | 10/2003 | Ferree |
| 2003/0199983 A1 | 10/2003 | Michelson |
| 2003/0204260 A1 | 10/2003 | Ferree |
| 2003/0208271 A1 | 11/2003 | Kuras |
| 2003/0208273 A1 | 11/2003 | Eisermann et al. |
| 2003/0208274 A1 | 11/2003 | Davis |
| 2003/0216744 A1 | 11/2003 | Longhini et al. |
| 2003/0216810 A1 | 11/2003 | Ralph et al. |
| 2003/0220690 A1 | 11/2003 | Cauthen |
| 2003/0220694 A1 | 11/2003 | Cauthen |
| 2003/0225408 A1 | 12/2003 | Nichols et al. |
| 2003/0225416 A1 | 12/2003 | Bonvallet et al. |
| 2003/0229358 A1 | 12/2003 | Errico et al. |
| 2003/0229397 A1 | 12/2003 | Davis |
| 2003/0233097 A1 | 12/2003 | Ferree |
| 2003/0233145 A1 | 12/2003 | Landry et al. |
| 2003/0233148 A1 | 12/2003 | Ferree |
| 2003/0236520 A1 | 12/2003 | Lim et al. |
| 2004/0002758 A1 | 1/2004 | Landry et al. |
| 2004/0002759 A1 | 1/2004 | Ferree |
| 2004/0002761 A1 | 1/2004 | Rogers et al. |
| 2004/0002762 A1 | 1/2004 | Hawkins |
| 2004/0006343 A1 | 1/2004 | Sevrain |
| 2004/0010254 A1 | 1/2004 | Cook et al. |
| 2004/0010316 A1 | 1/2004 | William et al. |
| 2004/0021042 A1 | 2/2004 | Stephen et al. |
| 2004/0022582 A1 | 2/2004 | Sick |
| 2004/0024406 A1 | 2/2004 | Ralph et al. |
| 2004/0024407 A1 | 2/2004 | Ralph et al. |
| 2004/0024459 A1 | 2/2004 | Ferree |
| 2004/0024461 A1 | 2/2004 | Ferree |
| 2004/0024462 A1 | 2/2004 | Ferree et al. |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0034426 A1 | 2/2004 | Errico et al. |
| 2004/0039387 A1 | 2/2004 | Gause et al. |
| 2004/0068318 A1 | 4/2004 | Coates et al. |
| 2004/0068320 A1 | 4/2004 | Robie et al. |
| 2004/0073311 A1 | 4/2004 | Ferree |
| 2004/0078079 A1 | 4/2004 | Foley |
| 2004/0092932 A1 | 5/2004 | Aubin et al. |
| 2004/0106927 A1 | 6/2004 | Ruffner et al. |
| 2004/0117022 A1 | 6/2004 | Marnay et al. |
| 2004/0133281 A1 | 7/2004 | Khandkar et al. |
| 2004/0138750 A1 | 7/2004 | Mitchell |
| 2004/0143270 A1 | 7/2004 | Zucherman et al. |
| 2004/0143332 A1 | 7/2004 | Krueger et al. |
| 2004/0148028 A1 | 7/2004 | Ferree et al. |
| 2004/0167628 A1 | 8/2004 | Foley |
| 2004/0176772 A1 | 9/2004 | Zubok et al. |
| 2004/0176773 A1 | 9/2004 | Zubok et al. |
| 2004/0176774 A1 | 9/2004 | Zubok et al. |
| 2004/0176777 A1 | 9/2004 | Zubok et al. |
| 2004/0176778 A1 | 9/2004 | Zubok et al. |
| 2004/0176843 A1 | 9/2004 | Zubok et al. |
| 2004/0176852 A1 | 9/2004 | Zubok et al. |
| 2004/0193272 A1 | 9/2004 | Zubok et al. |
| 2004/0215198 A1 | 10/2004 | Marnay et al. |
| 2004/0220567 A1 | 11/2004 | Eisermann et al. |
| 2004/0220582 A1 | 11/2004 | Keller |
| 2004/0233148 A1 | 11/2004 | Tanghe et al. |
| 2004/0243240 A1 | 12/2004 | Beaurain et al. |
| 2004/0267369 A1 | 12/2004 | Lyons et al. |
| 2005/0021042 A1 | 1/2005 | Marnay et al. |
| 2005/0033430 A1 | 2/2005 | Powers et al. |
| 2005/0043800 A1 | 2/2005 | Paul et al. |
| 2005/0043803 A1 | 2/2005 | Schultz et al. |
| 2005/0055029 A1 | 3/2005 | Marik et al. |
| 2005/0071013 A1 | 3/2005 | Zubok et al. |
| 2005/0072822 A1 | 4/2005 | Stotts |
| 2005/0085917 A1 | 4/2005 | Marnay et al. |
| 2005/0113842 A1 | 5/2005 | Bertagnoli et al. |
| 2005/0119665 A1 | 6/2005 | Keller |
| 2005/0143749 A1 | 6/2005 | Zalenski et al. |
| 2005/0159819 A1 | 7/2005 | McCormack et al. |
| 2005/0165406 A1 | 7/2005 | Assell et al. |
| 2005/0165487 A1 | 7/2005 | Muhanna et al. |
| 2005/0197705 A1 | 9/2005 | Arnin et al. |
| 2005/0203533 A1 | 9/2005 | Ferguson et al. |
| 2005/0228497 A1 | 10/2005 | Ferree et al. |
| 2005/0228500 A1 | 10/2005 | Kim et al. |
| 2005/0240270 A1 | 10/2005 | Zubok et al. |
| 2005/0240271 A1 | 10/2005 | Zubok et al. |
| 2005/0240272 A1 | 10/2005 | Zubok et al. |
| 2005/0240273 A1 | 10/2005 | Khandkar et al. |
| 2005/0256577 A1 | 11/2005 | Baumgartner et al. |
| 2005/0267581 A1 | 12/2005 | Marnay et al. |
| 2005/0267582 A1 | 12/2005 | Ferree et al. |
| 2005/0283237 A1 | 12/2005 | Zucherman et al. |
| 2006/0004377 A1 | 1/2006 | Keller |
| 2006/0030857 A1 | 2/2006 | de Villiers et al. |
| 2006/0036326 A1 | 2/2006 | Baumgartner et al. |
| 2006/0064100 A1 | 3/2006 | Bertagnoli et al. |
| 2006/0069439 A1 | 3/2006 | Zucherman et al. |
| 2006/0085077 A1 | 4/2006 | Cook et al. |
| 2006/0100634 A1 | 5/2006 | Ferguson |
| 2006/0116768 A1 | 6/2006 | Krueger et al. |
| 2006/0129160 A1 | 6/2006 | Liu et al. |
| 2006/0149273 A1 | 7/2006 | Ross et al. |
| 2006/0149278 A1 | 7/2006 | Abdou |
| 2006/0167461 A1 | 7/2006 | Hawkins et al. |
| 2006/0178748 A1 | 8/2006 | Dinger et al. |
| 2006/0195114 A1 | 8/2006 | Bertagnoli |
| 2006/0200166 A1 | 9/2006 | Hanson et al. |
| 2006/0217731 A1 | 9/2006 | Gil et al. |
| 2006/0235422 A1 | 10/2006 | Keller |
| 2006/0247645 A1 | 11/2006 | Wilcox et al. |
| 2006/0247649 A1 | 11/2006 | Rezach et al. |
| 2006/0282020 A1 | 12/2006 | Bertagnoli et al. |
| 2007/0073403 A1 | 3/2007 | Lombardo et al. |
| 2007/0073405 A1 | 3/2007 | Verhulst et al. |
| 2007/0106388 A1 | 5/2007 | Michelson |
| 2007/0112429 A1 | 5/2007 | Muhanna et al. |
| 2007/0118145 A1 | 5/2007 | Fischer et al. |
| 2007/0118224 A1 | 5/2007 | Shah et al. |
| 2007/0123989 A1 | 5/2007 | Gfeller et al. |
| 2007/0191856 A1 | 8/2007 | Gil et al. |
| 2007/0213820 A1 | 9/2007 | Magerl et al. |
| 2007/0225813 A1 | 9/2007 | Haines |
| 2007/0265707 A1 | 11/2007 | Marnay et al. |
| 2007/0282448 A1 | 12/2007 | Abdou |
| 2008/0027548 A9 | 1/2008 | Ferree et al. |
| 2008/0033563 A1 | 2/2008 | Khandkar et al. |

| | | |
|---|---|---|
| 2008/0077155 A1 | 3/2008 | Diederich et al. |
| 2008/0082169 A1 | 4/2008 | Gittings et al. |
| 2009/0018663 A1 | 1/2009 | Cook et al. |

FOREIGN PATENT DOCUMENTS

| | | |
|---|---|---|
| DE | 43 15 757 | 11/1994 |
| DE | 199 03 763 A1 | 8/2000 |
| DE | 10130825 | 3/2002 |
| EP | 0 392 076 A1 | 10/1990 |
| EP | 0 599 419 A2 | 6/1994 |
| EP | 599419 A2 | 6/1994 |
| EP | 1 222 903 A1 | 7/2002 |
| EP | 1219266 A1 | 7/2002 |
| FR | 2 718 635 A1 | 10/1995 |
| FR | 2 730 159 A1 | 8/1996 |
| FR | 2 805 985 A1 | 9/2001 |
| FR | 2 824 261 A1 | 11/2002 |
| RU | 1560184 | 4/1990 |
| RU | 2 077 288 C1 | 4/1997 |
| WO | 91/13598 A1 | 9/1991 |
| WO | 94/04100 A1 | 3/1994 |
| WO | 9509587 A1 | 4/1995 |
| WO | 97/10776 A2 | 3/1997 |
| WO | 9710780 A1 | 3/1997 |
| WO | 0024342 A1 | 5/2000 |
| WO | 0101893 A1 | 1/2001 |
| WO | 01/62191 A2 | 8/2001 |
| WO | 01/93785 | 12/2001 |
| WO | 01/93786 A2 | 12/2001 |
| WO | 03/084449 A1 | 10/2003 |
| WO | 03090649 A1 | 11/2003 |
| WO | 2004/019828 A1 | 3/2004 |
| WO | 2004/026186 A1 | 4/2004 |

SPACERLESS ARTIFICIAL DISC REPLACEMENTS

REFERENCE TO RELATED APPLICATION

This application is a continuation of U.S. application Ser. No. 11/194,786 ("the '786 Application") filed Aug. 1, 2005, now abandoned, which claims the benefit of the filing date of U.S. Provisional Patent Application No. 60/372,520, filed Apr. 12, 2002 and is a continuation of U.S. application Ser. No. 10/413,028 ("the '028 Application") filed on Apr. 14, 2003, now abandoned, the disclosures of which are incorporated herein by reference. This application, the '786 Application, and the '028 Application also claim the benefit of U.S. Provisional Patent Application No. 60/449,642 filed Feb. 24, 2003.

FIELD OF THE INVENTION

This invention relates generally to artificial disc replacements (ADRs) and, more particularly, to devices that operate without softer spacer materials such as polyethylene.

BACKGROUND OF THE INVENTION

Polyethylene spacers are common in some artificial joint situations, including total knee replacements (TKRs). Polyethylene spacers are also used between metal plates in many artificial disc replacement (ADR) designs.

Complications arising from poly debris are well documented, however, including fracture of the spacer once it becomes too thin, absorptions and migration of poly particles throughout the body, and loosening of the bone metal junction as a reaction of the poly debris.

Metal-on-metal and ceramic-on-metal surfaces have much lower wear characteristics. In fact, metal-on-metal surfaces demonstrate 400 times less wear than polyethylene on metal surfaces.

While there have been attempts to limit the use of the poly in ADR designs, all existing approaches constitute call-and-socket configurations which do not inherently limit axial rotation. Instead, axial rotation is limited through the use of multiple ball-and-socket joints or an elongated ball-and-socket joint, which complicates the design.

SUMMARY OF THE INVENTION

The present invention replaces polyethylene artificial disc replacement (ADR) spacers with harder, more wear resistant materials. In the preferred embodiments, an ADR according to the invention includes opposing saddle-shaped components to facilitate more normal spinal flexion, extension, and lateral bending. Preferably, the ADR allows at least 10 degrees of movement on the flexion to extension direction and at least 5 degrees of movement in the lateral bending direction. The saddle-shaped articulating surfaces also limit axial rotation, thereby protecting the facet joints and the annulus fibrosis (AF).

According to the invention, either or both the superior and inferior components are made of a hard material such as chrome cobalt, titanium, or a ceramic including alumina, zirconia, or calcium phosphate. The articulating surfaces of the ADR are also preferably highly polished to reduce friction between the components. Metals, alloys or other materials with shape-memory characteristics may also prove beneficial.

The vertebral surfaces of the components may be treated to promote bone ingrowth. For example, the vertebral surfaces of the components may have plasma spray or beads. Alternatively, one or both components may be cemented to the vertebrae. The vertebra-facing surfaces may also include projections such as keels that fit into the vertebrae. In embodiments adapted for cementation, one of the components could be made of polyethylene or other softer material.

DETAILED DESCRIPTION OF THE INVENTION

Figure 1A:
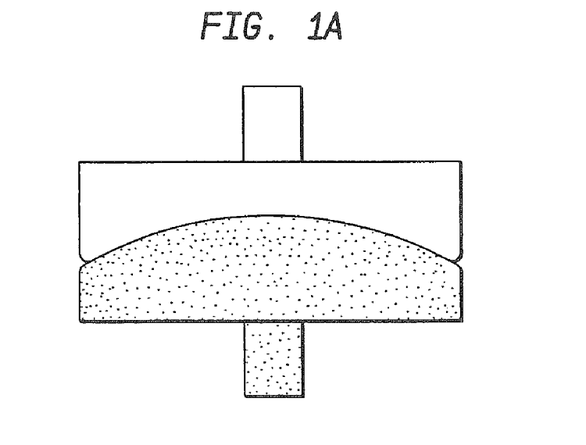
FIG. 1A is an anterior view of an ADR according to the invention.
Figure 1B:
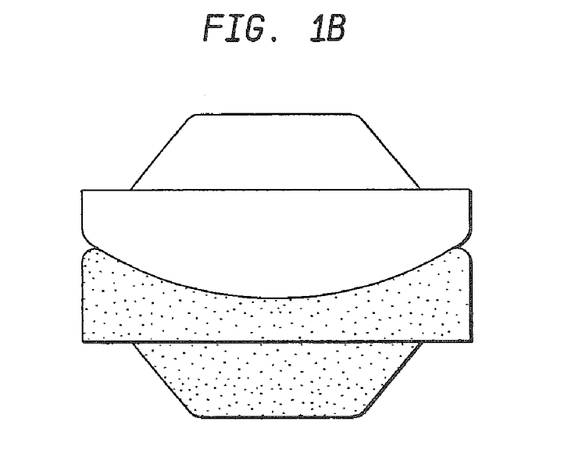
FIG. 1B is a lateral view of the ADR of FIG. 1.
Figure 1C:
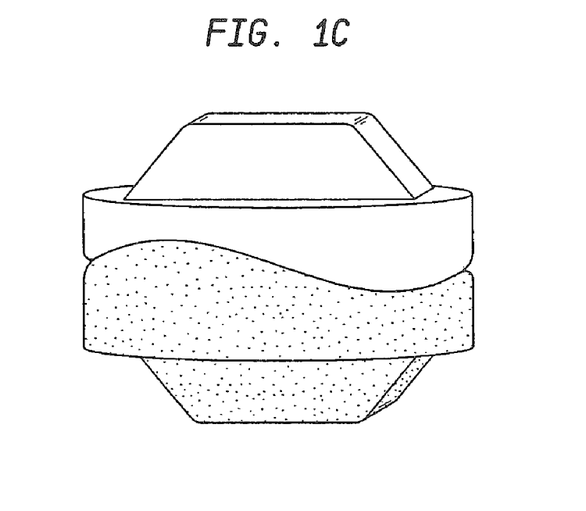
FIG. 1C is an oblique view of the ADR of FIG. 1.

FIG. 1A is an anterior view of an ADR according to the invention. FIG. 1B is a lateral view of the ADR of FIG. 1. FIG. 1C is an oblique view of the ADR of FIG. 1.

Figure 2A:
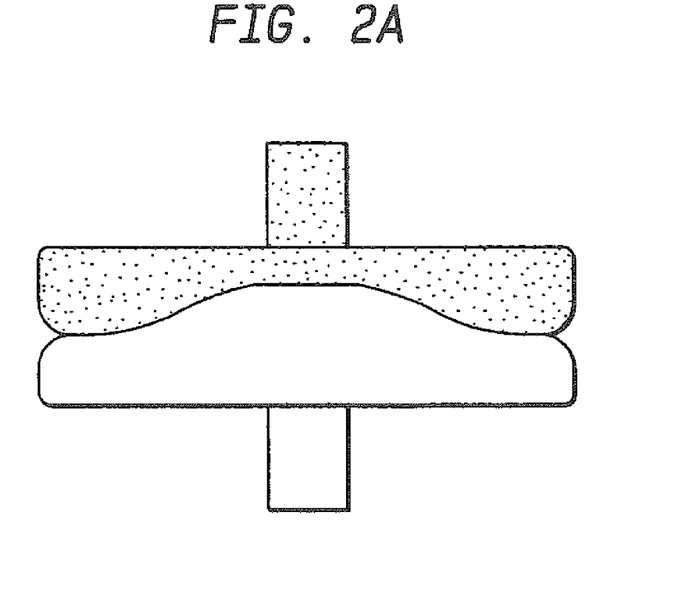
FIG. 2A is a view of the anterior aspect of an alternative embodiment of the ADR.
Figure 2B:
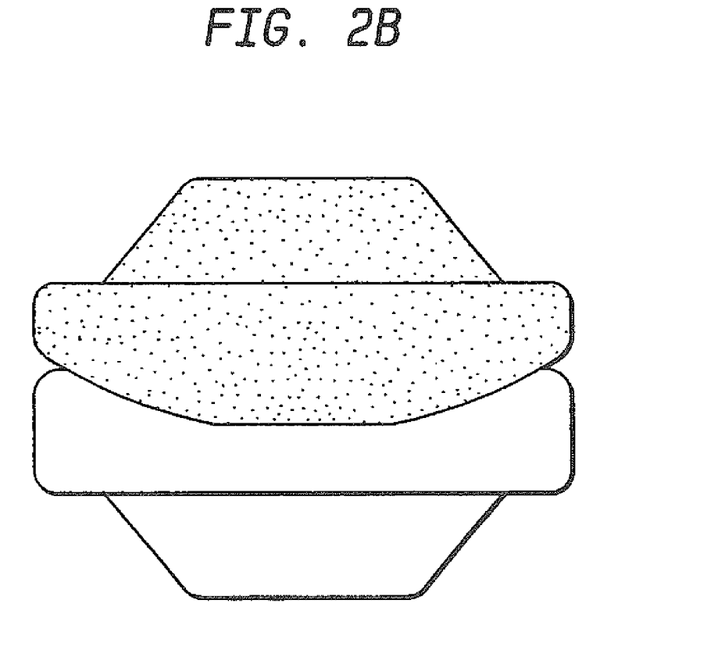
FIG. 2B is a view of the lateral aspect of an alternative embodiment of the ADR shown in FIG. 2B.

FIG. 2A is a view of the anterior aspect of an alternative embodiment of the ADR, wherein the articulating surfaces of both components have a flat area centrally from the front to the back of the ADR. FIG. 2B is a view of the lateral aspect of an alternative embodiment of the ADR drawn in FIG. 2B. The flat area of the articulating surfaces courses centrally from side of the DR to the other side. The flat area allows one component to translate slightly on the other component. Alternatively, a curved area with a large radius could replace the flat area.

Figure 3A:
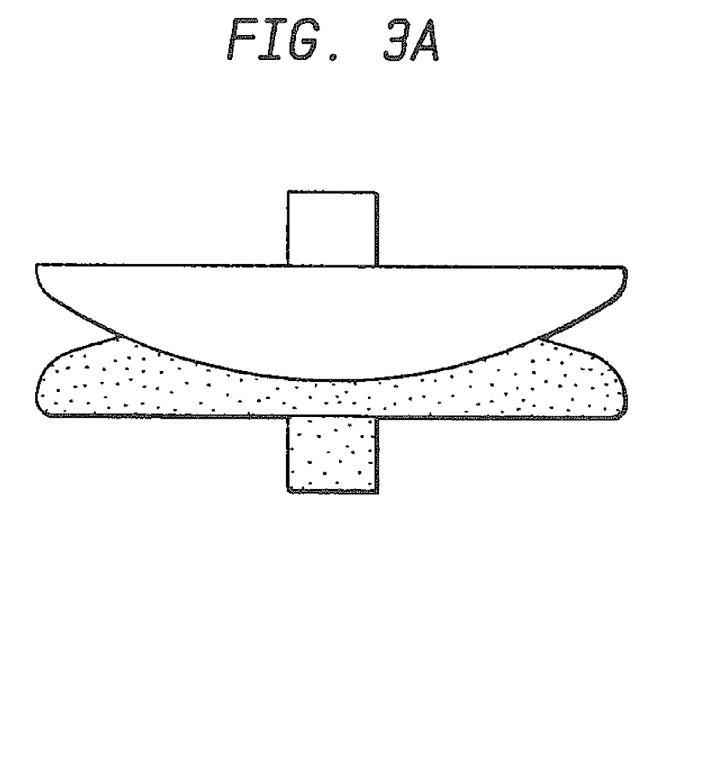
FIG. 3A is a view of the anterior aspect of an alternative, less constrained, embodiment of the saddle-shaped ADR shown in a fully flexed position.
Figure 3B:
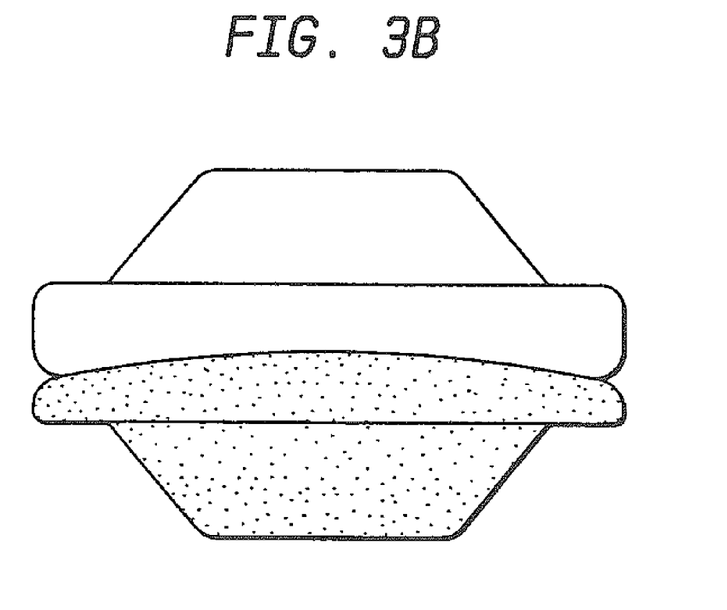
FIG. 3B is a view of the lateral aspect of the embodiment of the ADR shown in FIG. 3A.

FIG. 3A is a view of the anterior aspect of an alternative, less constrained, embodiment of the saddle-shaped ADR drawn in a fully flexed position. The less constrained embodiment facilitates spinal flexion, extension, and lateral bending. FIG. 3B is a view of the lateral aspect of the embodiment of the ADR drawn in FIG. 3A.

Figure 4A:
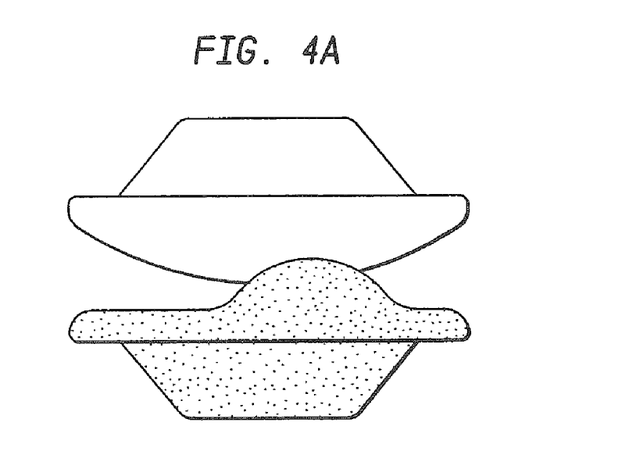
FIG. 4A is a view of the lateral aspect of another embodiment of a saddle-shaped ADR.
Figure 4B:
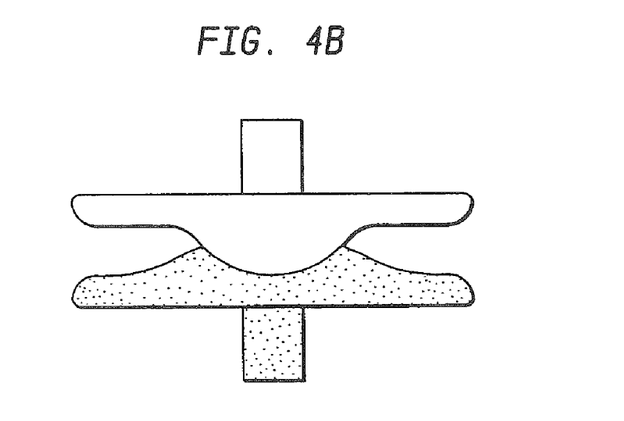
FIG. 4B is a view of the anterior aspect of the embodiment of the ADR shown in FIG. 4A in a fully flexed position.

FIG. 4A is a view of the lateral aspect of another embodiment of a saddle-shaped ADR. The center of rotation for flexion and extension is not necessarily located in the center of the ADR. For example, the center of rotation is preferably located in the posterior half of the ADR. FIG. 4B is a view of the anterior aspect of the embodiment of the ADR drawn in FIG. 4A, drawn in a fully flexed position.

Figure 4C:
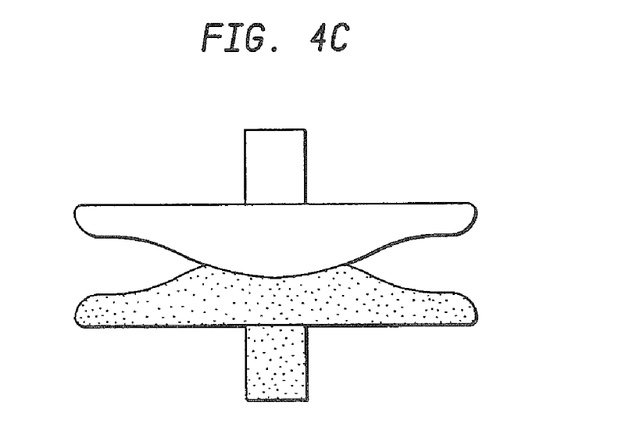
FIG. 4C is a view of the anterior aspect of an alternative embodiment.

FIG. 4C is a view of the anterior aspect of an alternative embodiment, showing how the radius of curvature of the articulation for lateral bending may be different than the radius of curvature for articulation for flexion and extension.

For example, the radius of curvature for the articulation for flexion and extension, as seen in FIG. 4A, may be smaller than the radius of curvature for the articulation for lateral bending, as seen in FIG. 4C. Articulating surfaces with smaller radii, facilitate movement. Thus, the embodiment of the ADR drawn in FIG. 4A flexes and extends more easily than the embodiment of the ADR drawn in FIG. 3A. The ADR is drawn in a fully flexed position.

Figure 4D:
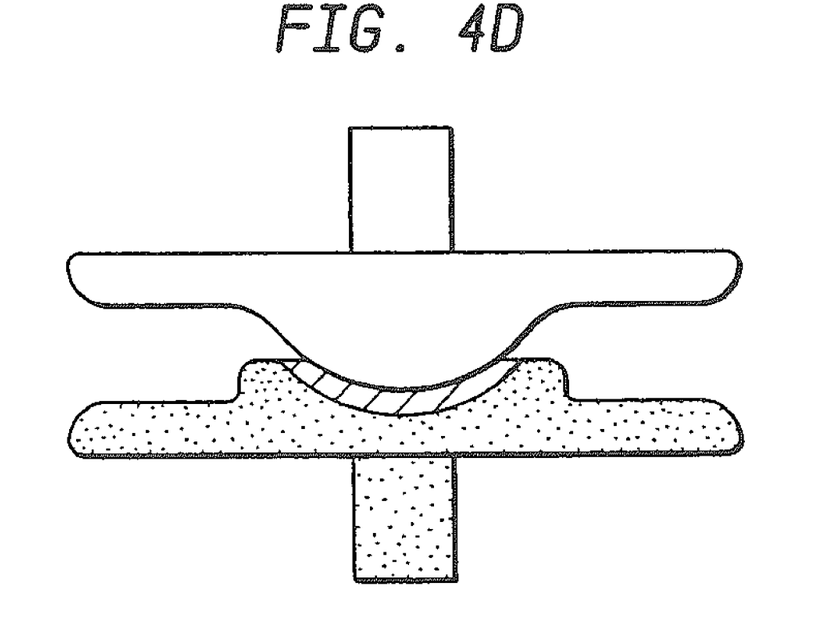
FIG. 4D is a view of the anterior aspect of the ADR shown in FIG. 4A.
Figure 4E:
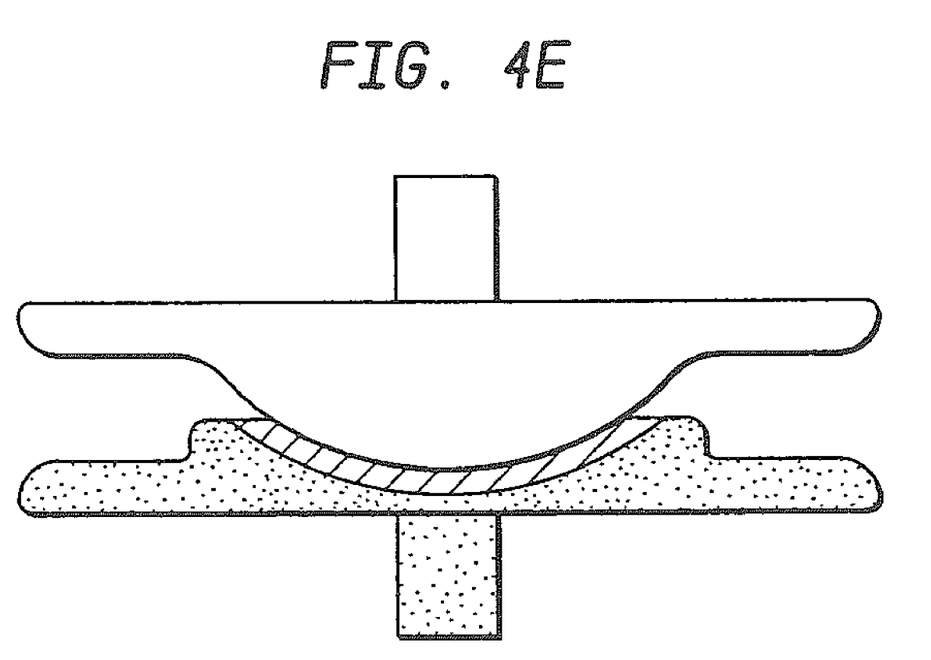
FIG. 4E is a view of the anterior aspect of the ADR shown in FIG. 4A.

FIG. 4D is a view of the anterior aspect of the ADR drawn in FIG. 4A. The ADR is drawn in a neutral position. The area of the drawing with diagonal lines represents the articulating surface of the lower ADR component. FIG. 4E is a view of the anterior aspect of the ADR drawn in FIG. 4A, also drawn in a fully extend position.

The invention claimed is:

1. An artificial disc replacement comprising:
a first component having a first articulating surface and a first vertebral contact surface for engaging a first vertebral body, the first vertebral contact surface including at least one projection for engaging the first vertebral body, and the first articulating surface including first and second lateral edges and a toroidal region extending between the first lateral edge and the second lateral edge; and
a second component having a second articulating surface engaged with the first articulating surface and a second vertebral contact surface for engaging a second vertebral body, the second vertebral contact surface including at least one projection for engaging the second vertebral body, and the second articulating surface including third and fourth lateral edges and a toroidal region extending between the third lateral edge and the fourth lateral edge,
wherein the toroidal region of the first and second articulating surfaces, respectively, are defined by continuous curves,
wherein the first articulating surface is located in at least an anterior portion of the first component, and the second articulating surface is located in at least a posterior portion of the second component,
and wherein the first articulating surface is defined by a concave arc having a radius of curvature A about a first axis, and a convex arc having a radius of curvature B about a second axis perpendicular to the first axis, and the second articulating surface is defined by a convex arc having a radius of curvature C about a third axis, and a concave arc having a radius of curvature D about a fourth axis perpendicular to the third axis.

2. The artificial disc replacement of claim 1, wherein the first and second articulating surfaces include congruent surfaces.

3. The artificial disc replacement of claim 1, wherein the at least one projection is selected from the group consisting of flanges and keels.

4. The artificial disc replacement of claim 3, wherein the keels extend from the first and second vertebral contact surface of the first and second component, respectively.

5. The artificial disc replacement of claim 1, wherein the first articulating surface includes a single substantially continuous concave surface and a single substantially continuous convex surface, and the second articulating surface includes a single substantially continuous concave surface and a single substantially continuous convex surface.

6. An artificial disc replacement comprising:
a first component having a first articulating surface and a first vertebral contact surface for engaging a first vertebral body, the first vertebral contact surface including at least one projection for engaging the first vertebral body, and the first articulating surface having a toroidal region with a first continuous convex arc and a first continuous concave arc, wherein the first articulating surface is defined by first and second lateral edges, the first continuous concave arc spanning between the first and the second lateral edge; and
a second component having a second articulating surface engaged with the first articulating surface and a second vertebral contact surface for engaging a second vertebral body, the second vertebral contact surface including at least one projection for engaging the second vertebral body, and the second articulating surface having a toroidal region with a second continuous convex arc and a second continuous concave arc,
wherein the first articulating surface is located in at least an anterior portion of the first component, and the second articulating surface is located in at least a posterior portion of the second component,
and wherein the first concave arc has a radius of curvature A about a first axis, and the first convex arc has a radius of curvature B about a second axis perpendicular to the first axis, and the second convex arc has a radius of curvature C about a third axis, and the second concave arc has a radius of curvature D about a fourth axis perpendicular to the third axis.

7. The artificial disc replacement of claim 6, wherein the first and second articulating surfaces include congruent surfaces.

8. The artificial disc replacement of claim 6, wherein the at least one projection is selected from the group consisting of flanges and keels.

9. The artificial disc replacement of claim 8, wherein the keels extend from the first and second vertebral contact surface of the first and second component, respectively.

* * * * *